(12) United States Patent
Gupta et al.

(10) Patent No.: US 7,521,237 B2
(45) Date of Patent: Apr. 21, 2009

(54) METHODS FOR PROMOTING MATURATION OF CONIFER SOMATIC EMBRYOS

(75) Inventors: Pramod K. Gupta, Federal Way, WA (US); Bonnie Larson, Granite Falls, WA (US); Diane Holmstrom, Sumner, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 617 days.

(21) Appl. No.: 10/861,168

(22) Filed: Jun. 4, 2004

(65) Prior Publication Data

US 2005/0003415 A1    Jan. 6, 2005

Related U.S. Application Data

(60) Provisional application No. 60/480,942, filed on Jun. 23, 2003.

(51) Int. Cl.
*C12N 5/00* (2006.01)
(52) U.S. Cl. ..................................................... 435/422
(58) Field of Classification Search .................. 435/422
See application file for complete search history.

(56) References Cited

U.S. PATENT DOCUMENTS

| | | | |
|---|---|---|---|
| 4,217,730 A | 8/1980 | Abo El-Nil | |
| 4,801,545 A | 1/1989 | Stuart et al. | |
| 4,957,866 A | 9/1990 | Gupta et al. | |
| 5,034,326 A | 7/1991 | Pullman et al. | |
| 5,036,007 A | 7/1991 | Gupta et al. | |
| 5,041,382 A | 8/1991 | Gupta et al. | |
| 5,183,757 A | 2/1993 | Roberts | |
| 5,187,092 A | 2/1993 | Uddin | |
| 5,236,841 A | 8/1993 | Gupta et al. | |
| 5,238,835 A | 8/1993 | McKersie et al. | |
| 5,294,549 A | 3/1994 | Pullman et al. | |
| 5,413,930 A | 5/1995 | Becwar et al. | |
| 5,464,769 A | 11/1995 | Attree et al. | |
| 5,482,857 A | 1/1996 | Gupta et al. | |
| 5,491,090 A | 2/1996 | Handley, III et al. | |
| 5,501,972 A | 3/1996 | Westcott | |
| 5,506,136 A | 4/1996 | Becwar et al. | |
| 5,523,230 A | 6/1996 | Smith | |
| 5,534,433 A | 7/1996 | Coke | |
| 5,534,434 A | 7/1996 | Coke | |
| 5,563,061 A | 10/1996 | Gupta | |
| 5,564,224 A | 10/1996 | Carlson et al. | |
| 5,565,355 A | 10/1996 | Smith | |
| 5,587,312 A | 12/1996 | van Holst et al. | |
| 5,610,051 A | 3/1997 | Becwar et al. | |
| 5,677,185 A | 10/1997 | Handley, III | |
| 5,731,191 A | 3/1998 | Rutter et al. | |
| 5,731,203 A | 3/1998 | Handley, III | |
| 5,731,204 A | 3/1998 | Rutter et al. | |
| 5,821,126 A | 10/1998 | Durzan et al. | |
| 5,840,581 A | 11/1998 | Carraway et al. | |
| 5,850,032 A | 12/1998 | Wann | |
| 5,856,191 A | 1/1999 | Handley, III | |
| 5,985,667 A | 11/1999 | Attree et al. | |
| 6,022,744 A | 2/2000 | Tetteroo et al. | |
| 6,117,678 A | 9/2000 | Carpenter et al. | |
| 6,134,830 A | 10/2000 | Welty | |
| 6,150,167 A | 11/2000 | Carpenter et al. | |
| 6,180,405 B1 | 1/2001 | Aitken-Christie et al. | |
| 6,200,809 B1 | 3/2001 | Klimaszewska et al. | |
| 6,340,594 B1 | 1/2002 | Attree et al. | |
| 6,372,496 B1 | 4/2002 | Attree et al. | |
| 6,417,001 B2 | 7/2002 | Aitken-Christie et al. | |
| 6,444,467 B1 | 9/2002 | Fan et al. | |
| 6,492,174 B1 | 12/2002 | Pullman et al. | |
| 2002/0012994 A1 | 1/2002 | Aitken-Christie et al. | |
| 2002/0092037 A1 | 7/2002 | Connett-Porceddu et al. | |
| 2002/0100083 A1 | 7/2002 | Connett-Porceddu et al. | |

FOREIGN PATENT DOCUMENTS

| | | |
|---|---|---|
| EP | 0 300 730 B1 | 1/1989 |
| EP | 0 618 766 B1 | 10/1994 |
| EP | 0 934 691 A2 | 8/1999 |
| NZ | 270706 | 10/1996 |
| NZ | 270707 | 2/1997 |
| NZ | 314791 | 6/1999 |

(Continued)

OTHER PUBLICATIONS

Helena Lipavska and Hana Konradova. Somatic Embryogenesis in conifers:The role of Carbohydrate Metabolism. In Vitro Cell Dev. Bio._Plant 40:Jan.-Feb. 23-30, 2004.*

(Continued)

*Primary Examiner*—Annette H Para
(74) *Attorney, Agent, or Firm*—Christensen O'Connor Johnson Kindness

(57) ABSTRACT

In one aspect, the present invention provides methods for producing mature conifer somatic embryos. The methods of the invention comprise the steps of: (a) culturing pre-cotyledonary conifer somatic embryos in, or on, a development medium comprising less than 0.5% of gellan gum to form cotyledonary conifer somatic embryos; and (b) culturing cotyledonary conifer somatic embryos formed in step (a) in, or on, a maturation medium comprising between about 0.5% to about 1.5% of gellan gum to form mature conifer somatic embryos. In some embodiments, the maturation medium further comprises sucrose and/or abscisic acid.

14 Claims, No Drawings

FOREIGN PATENT DOCUMENTS

| | | |
|---|---|---|
| WO | WO 95/33822 A1 | 12/1995 |
| WO | WO 98/48279 A1 | 10/1998 |
| WO | WO 99/46977 | 9/1999 |
| WO | WO 01/20972 A1 | 9/2000 |

OTHER PUBLICATIONS

Percy Re et al, "Evaluation of somatic embryogenesis for clonal propagation of western white pine," *Can J For Res* 30(12): 1867-1876.

Ramarosandtradana LH et al, "Effects of Carbohydrate Source, Polyethylene Glycol and Gellan Gum Concentration on Embryonal-Suspensor Mass (ESM) Proliferation and Maturation of Maritime Pine Somatic Embryos," *In vitro Cellular and Developmental Biology-Plant* 37:29-34.

Ramarosandtradana LH et al, "Effects of Carbohydrate Source, Polyethylene Glycol and Gellan Gum Concentration on Embryonal-Suspensor Mass (ESM) Proliferation and Maturation of Maritime Pine Somatic Embryos," *In vitro Cellular and Developmental Biology-Plant* 37:29-34.

Klimaszewska K et al, "Maturation of somatic embryos of pinus strobes is promoted by a high concentration of gellan gum," *Physiologica Plantarum* (100) 949-957, 1997.

Garin E et al, "Effects of sugars, amino acids, and culture technique on maturation of somatic embryos of Pinus strobes on medium with two gellan gum concentrations," *Plant Cell Tiss & Org Cult* (62) 27-27, 2000.

Lelu Ma et al, "Somatic embryogenesis and plantlet development in Pinus sylvestris and pinus pinaster on median with and without growth regulators," *Phys Plantarum, Munksgaard Intl* (105) 719-718, 1999.

Taber RP et al., "Kinetics of Douglas-fir (Pseudotsungo menziesii) somatic embryo development," *Can J Bot* (76): 838-871, 1998.

Attree, S.M. et al., "Somatic Embryo Maturation, Germination, and Soil Establishment of Plants of Black and White Spruce (Picea mariana and Picea glauca)," Can. J. Bot. 68:2583-2589, 1990.

Boulay, M.P., et al., "Development of Somatic Embryos From Cell Suspension Cultures of Norway Spruce (Picea abies Karst.)," Plant Cell Reports 7:134-137, 1988.

Gupta, P.K., et al., "Scale-Up Somatic Embryogenesis of Conifers For Reforestation," Proceedings of the 3rd Canadian Workshop on Plant Tissue Culture and Genetic Engineering, University of Guelph, Symposium 1: Somatic Embryogenesis and Synthetic Seeds, Abstract, Jun. 1992.

Jain, S.M., et al., Forestry Sciences: Somatic Embryogenesis in Woody Plants, vol. 3, Gymnosperms, Kluwer Academic Publishers, Netherlands, 1995.

Keinonen-Mettälä, K., et al., "Somatic Embryogenesis of Pinus sylvestris," Scand. J. For. Res. 11:242-250, 1996.

Mathur, G. et al., "Studies on Somatic Embryogenesis From Immature Zygotic Embryos of CHIR Pine (Pinus roxburghii Sarg.)," Current Science 79(7):999-1004, 2000.

Timmis, R., "Bioprocessing for Tree Production in the Forest Industry: Conifer Somatic Embryogenesis," Biotechnol. Prog. 14(1):156-166, 1998.

Von Aderkas, P., et al., "Charcoal Affects Early Development and Hormonal Concentrations of Somatic Embryos of Hybrid Larch," Tree Physiology 22:431-434, 2002.

Nagmani, R., et al., "Anatomical Comparison of Somatic and Zygotic Embryogeny in Conifers," in Jain, S.M., Gupta, Pramod K., and Newton, R.J. (eds.), Somatic Embryogenesis in Woody Plants, vol. I, Series: Forestry Sciences, 1995, pp. 23-48.

* cited by examiner

METHODS FOR PROMOTING MATURATION OF CONIFER SOMATIC EMBRYOS

CROSS-REFERENCE TO RELATED APPLICATION

This application claims the benefit of U.S. Provisional Application No. 60/480,942, filed Jun. 23, 2003.

FIELD OF THE INVENTION

The present invention relates to methods for producing plant embryos in vitro, and optionally producing plants from the plant embryos.

BACKGROUND OF THE INVENTION

The demand for coniferous trees, such as pines and firs, to make wood products continues to increase. One proposed solution to this problem is to identify individual trees that possess desirable characteristics, such as a rapid rate of growth, and produce numerous, genetically identical, clones of the superior trees by somatic cloning.

Somatic cloning is the process of creating genetically identical trees from tree tissue other than the male and female gametes. In one approach to somatic cloning, plant tissue is cultured in an initiation medium which includes hormones, such as auxins and/or cytokinins, that initiate formation of embryogenic cells that are capable of developing into somatic embryos. The embryogenic cells are then further cultured in a maintenance medium that promotes multiplication of the embryogenic cells to form pre-cotyledonary embryos (i.e., embryos that do not possess cotyledons). The multiplied embryogenic cells are then cultured in a development medium that promotes development of cotyledonary somatic embryos which can, for example, be placed within artificial seeds and sown in the soil where they germinate to yield conifer seedlings. The seedlings can be transplanted to a growth site for subsequent growth and eventual harvesting to yield lumber, or wood-derived products.

A continuing problem with somatic cloning of conifer embryos is stimulating efficient formation of somatic embryos that are capable of germinating to yield plants. Preferably conifer somatic embryos, formed in vitro, are physically and physiologically similar, or identical, to conifer zygotic embryos formed in vivo in conifer seeds. There is therefore a continuing need for methods for producing viable conifer somatic embryos from conifer embryogenic cells.

SUMMARY OF THE INVENTION

In one aspect, the present invention provides methods for producing mature conifer somatic embryos. The methods of the invention comprise the steps of: (a) culturing pre-cotyledonary conifer somatic embryos in, or on, a development medium comprising less than 0.5% of gellan gum to form cotyledonary conifer somatic embryos; and (b) culturing cotyledonary conifer somatic embryos formed in step (a) in, or on, a maturation medium comprising between about 0.5% to about 1.5% of gellan gum to form mature conifer somatic embryos. In some embodiments, the maturation medium further comprises sucrose and/or abscisic acid.

A population of mature conifer somatic embryos produced according to the methods of the invention has a greater efficiency of germinating into conifer plants than a population of conifer somatic embryos produced according to an otherwise identical control method that does not include the step of culturing cotyledonary conifer somatic embryos in, or on, a maturation medium comprising between about 0.5% to about 1.5% of gellan gum to form mature conifer somatic embryos. Some embodiments of the methods of the invention yield mature conifer somatic embryos that have an efficiency of germinating into plants that is at least double the germination efficiency of the foregoing control method.

The methods of the present invention are useful for preparing mature conifer somatic embryos that can be further characterized, such as by genetic or biochemical means, and/or can be germinated to yield conifers, if so desired. Thus, for example, the methods of the invention can be used to produce clones of individual conifers that possess one or more desirable characteristics, such as a rapid growth rate or improved wood quality. For example, a population of mature conifer somatic embryos of the invention can be used to produce a stand, or forest, of conifers possessing one or more desirable characteristics, such as a rapid growth rate or improved wood quality. The trees can be utilized to produce wood products.

In another aspect, the present invention provides mature conifer somatic embryos produced according to the methods of the invention.

DETAILED DESCRIPTION OF THE PREFERRED EMBODIMENT

Unless specifically defined herein, all terms used herein have the same meaning as they would to one skilled in the art of the present invention.

As used herein, the term "cotyledonary embryo" refers to an embryo with a well-defined, elongated bipolar structure with latent meristematic centers having one or more clearly visible cotyledonary primordia at one end and a latent radicle at the opposite end. A "pre-cotyledonary embryo" refers to an embryo that does not yet have cotyledons.

Unless stated otherwise, all concentration values that are expressed as percentages are weight per volume percentages.

In one aspect, the present invention provides methods for producing mature conifer somatic embryos. The methods of the invention comprise the steps of: (a) culturing pre-cotyledonary conifer somatic embryos in, or on, a development medium comprising less than 0.5% of gellan gum to form cotyledonary conifer somatic embryos; and (b) culturing cotyledonary conifer somatic embryos formed in step (a) in, or on, a maturation medium comprising between about 0.5% to about 1.5% of gellan gum to form mature conifer somatic embryos. A mature conifer embryo according to the invention refers to an embryo that is capable of germinating into a plant. The methods of the invention can be used to produce cotyledonary somatic embryos from any conifer, such as members of the genus *Pinus*, such as Loblolly pine (*Pinus taeda*) and Radiata pine. Again, by way of example, Douglas fir embryos can be produced by the methods of the invention.

Pre-cotyledonary conifer somatic embryos can be prepared from conifer somatic cells, such as cells obtained from conifer zygotic embryos. For example, cells from conifer zygotic embryos can be induced by hormones to form embryonal suspensor cell masses (ESMs) that can be treated in accordance with the present invention to yield mature conifer somatic embryos. ESMs can be prepared, for example, from pre-cotyledonary embryos removed from seed. For example, the seed are surface sterilized before removing the pre-cotyledonary embryos, which are then cultured on, or in, an induction medium that permits formation of ESMs which include early stage embryos in the process of multiplication by budding and cleavage. ESMs are typically cultured in a maintenance medium to form pre-cotyledonary somatic embryos. Suitable induction and maintenance media are further described below.

In the methods of the invention, pre-cotyledonary somatic embryos are cultured in, or on, a development medium comprising less than 0.5% gellan gum that promotes the development of cotyledonary embryos. The development medium is typically a solid medium, although the development medium can be a liquid medium. The development medium typically contains nutrients that sustain the somatic embryos. Maltose may be included in the development medium as the principal or sole source of sugar for the somatic embryos. Useful maltose concentrations are within the range of from about 1% to about 2.5%.

Suitable development media typically do not include growth-promoting hormones, such as auxins and cytokinins. The development medium may contain gellan gum. Gellan gum is a gelling agent marketed, for example, under the names GELRITE and PHYTAGEL. If gellan gum is included in the development medium, it is present at a concentration less than about 0.5%, typically at a concentration from about 0% to about 0.4%.

The osmolality of the development medium can be adjusted to a value that falls within a desired range, such as from about 250 mM/Kg to about 450 mM/Kg. Typically, an osmolality of 350 mM or higher is advantageous. An example of a suitable development medium is medium $BM_3$ set forth in EXAMPLE 1 herein.

Pre-cotyledonary conifer somatic embryos may be cultured in, or on, a development medium comprising less than about 0.5% of gellan gum for a period of from 5 weeks to 12 weeks, such as from 8 weeks to 10 weeks, at a temperature of from 10° C. to 30° C., such as from 15° C. to 25° C., or such as from 20° C. to 23° C.

According to the methods of the invention, cotyledonary conifer somatic embryos are transferred from the development medium comprising less than about 0.5% of gellan gum and cultured in, or on, a maturation medium comprising between about 0.5% to about 1.5% of gellan gum to form mature conifer somatic embryos. Mature conifer somatic embryos produced according to the methods of the invention have a greater germination efficiency than conifer somatic embryos produced according to an otherwise identical method that does not include the step of culturing cotyledonary conifer somatic embryos in, or on, a maturation medium comprising between about 0.5% to about 1.5% of gellan gum to form mature conifer somatic embryos. The maturation medium can be a liquid or a solid medium. The maturation medium also may include nutrients that sustain the somatic embryos, and one or more agents for adjusting the osmolality of the medium to within a desired range, such as between 130-250 mOsmo/kg. The pH of the medium can also be adjusted to a desired value, such as between pH 5.5 and pH 5.8. Maltose may be included in the medium as the principal or sole source of metabolizable sugar. Useful maltose concentrations are within the range of about 1% to about 2.5%. The maturation medium may contain an absorbent composition, such as activated charcoal, as described above for the induction medium. An exemplary maturation medium is set forth as $BM_4$ in EXAMPLE 1.

In some embodiments, the maturation medium further comprises sucrose and/or abscisic acid. The concentration of abscisic acid in the maturation medium may be between 0.5 mg/L and 500 mg/L. In some embodiments of the methods of the invention, the concentration of abscisic acid in the maturation medium is between 1 mg/L and 100 mg/L. In some embodiments, the concentration of abscisic acid in the development medium is between 5 mg/L and 20 mg/L.

In some embodiments of the invention, the maturation medium contains sucrose as the principal or sole source of metabolizable sugar. Useful sucrose concentrations are within the range of about 1% to about 6%.

Cotyledonary conifer somatic embryos are typically cultured in a maturation medium comprising gellan gum at a concentration of between about 0.5% and 1.5%, and optionally comprising sucrose and/or abscisic acid for a period of from about 1 week to about 5 weeks, such as from 2 weeks to 4 weeks, at a temperature of from about 10° C. to about 30° C.

In some embodiments, cotyledonary embryos that have been cultured in a maturation medium are then cultured in, or on, a stratification medium for a period of about 2 weeks to about 6 weeks, at a temperature of from about 2° C. to about 10° C. Typically, the stratification medium is similar or identical to the maturation medium, but does not contain abscisic acid and has a lower concentration of gellan gum, typically less than about 0.5%. The stratification medium may contain sucrose as the principal or sole source of metabolizable sugar. An exemplary stratification medium is set forth as $BM_5$ in EXAMPLE 1.

In some embodiments, the present invention provides methods for producing mature conifer somatic embryos, comprising the steps of (a) culturing conifer somatic cells in, or on, an induction medium to yield embryogenic cells; (b) culturing the embryogenic cells prepared in step (a) in, or on, a maintenance medium to multiply the embryogenic cells and form pre-cotyledonary conifer somatic embryos; (c) culturing pre-cotyledonary conifer somatic embryos formed in step (b) in, or on, a development medium comprising less than 0.5% gellan gum to form cotyledonary conifer somatic embryos; and (d) culturing the cotyledonary conifer somatic embryos formed in step (c) in, or on, a maturation medium comprising between about 0.5% to about 1.5% of gellan gum to form mature conifer somatic embryos. The maturation medium may optionally comprise sucrose and/or abscisic acid.

Thus, in some embodiments, conifer somatic cells are cultured in, or on, an induction medium to yield embryogenic cells. Embryogenic cells are cells that are capable of producing one or more cotyledonary conifer somatic embryos and include, for example, conifer embryonal suspensor masses. The induction medium typically includes inorganic salts and organic nutrient materials. The osmolality of the induction medium is typically about 160 mg/kg or even lower, but it may be as high as 170 mM/kg. The induction medium typically includes growth hormones. Examples of hormones that can be included in the induction medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 10 mg/L.

The induction medium may contain an absorbent composition, especially when very high levels of growth hormones are used. The absorbent composition can be any composition that is not toxic to the embryogenic cells at the concentrations utilized in the practice of the present methods, and that is capable of absorbing growth-promoting hormones, and toxic compounds produced by the plant cells during embryo development, that are present in the medium. Non-limiting examples of useful absorbent compositions include activated charcoal, soluble poly(vinyl pyrrolidone), insoluble poly(vinyl pyrrolidone), activated alumina, and silica gel. The absorbent composition may be present in an amount, for example, of from about 0.1 g/L to about 5 g/L. An example of an induction medium useful in the practice of the present invention is medium $BM_1$, set forth in EXAMPLE 1 herein. The induction medium is typically solid, and may be solidified by inclusion of a gelling agent.

Conifer somatic cells are typically cultured in, or on, an induction medium for a period of from 3 weeks to 10 weeks, such as from 6 weeks to 8 weeks, at a temperature of from 10° C. to 30° C., such as from 15° C. to 25° C., or such as from 20° C. to 23° C.

The maintenance medium may be a solid medium, or it may be a liquid medium which can be agitated to promote growth and multiplication of the embryogenic tissue. The osmolality of the maintenance medium is typically higher than the osmolality of the induction medium, typically in the range of 180-400 mM/kg. The maintenance medium may contain nutrients that sustain the embryogenic tissue, and may include hormones, such as one or more auxins and/or cytokinins, that promote cell division and growth of the embryogenic tissue. Typically, the concentrations of hormones in the maintenance medium is lower than their concentration in the induction medium.

It is generally desirable, though not essential, to include maltose as the sole, or principal, metabolizable sugar source in the maintenance medium. Examples of useful maltose concentrations are within the range of from about 1% to about 2.5%. An example of a suitable maintenance medium is medium $BM_2$ set forth in EXAMPLE 1 herein. Conifer embryogenic cells are typically transferred to fresh maintenance medium once per week.

As described above, pre-cotyledonary conifer somatic cells formed from conifer embryogenic cells are cultured in, or on, a development medium comprising less than 0.5% of gellan gum to form cotyledonary embryos. Cotyledonary embryos are further cultured in a maturation medium comprising between about 0.5% and about 1.5% gellan gum and optionally comprising sucrose and/or abscisic acid.

A population of mature conifer somatic embryos produced according to the methods of the invention has a greater germination efficiency than a population of conifer somatic embryos produced according to an otherwise identical method that does not include the step of culturing cotyledonary conifer somatic embryos in, or on, a maturation medium comprising between about 0.5% to about 1.5% of gellan gum to form mature conifer somatic embryos. Some embodiments of the methods of the invention yield mature conifer somatic embryos that have a germination efficiency that is at least 100% higher (e.g., between 100% and 200% higher) than the germination efficiency of mature conifer somatic embryos produced according to an otherwise identical method that does not include the step of culturing cotyledonary conifer somatic embryos in, or on, a maturation medium comprising between about 0.5% and 1.5% gellan gum.

The methods of the invention can be used, for example, to produce clones of individual conifer trees that possess one or more desirable characteristics, such as a rapid growth rate. Thus, in one aspect, the present invention provides methods for producing a population of genetically-identical, mature conifer somatic embryos. The methods of this aspect of the invention each include the steps of: (a) culturing genetically-identical pre-cotyledonary conifer somatic embryos in a development medium comprising less than 0.5% gellan gum to form cotyledonary embryos; and (b) culturing the cotyledonary conifer somatic embryos formed in step (a) in a maturation medium comprising between about 0.5% and about 1.5% gellan gum, and optionally further comprising sucrose and/or abscisic acid.

Another aspect of the invention provides mature conifer somatic embryos generated using the methods of the invention. The mature conifer somatic embryos produced using the methods of the invention can optionally be germinated to form conifer plants which can be grown into coniferous trees, if desired. Alternatively, the mature embryos may be disposed within artificial seeds for subsequent germination. The mature conifer somatic embryos can be germinated, for example, on a solid germination medium, such as medium $BM_6$ medium set forth in EXAMPLE 1 herein. The germinated plants can be transferred to soil for further growth. For example, the germinated plants can be planted in soil in a greenhouse and allowed to grow before being transplanted to an outdoor site. Typically, the mature conifer somatic embryos are illuminated to stimulate germination. Typically, all the steps of the methods of the invention, except germination, are conducted in the dark.

The following examples are provided for the purpose of illustrating, not limiting, the invention.

EXAMPLE 1

This Example shows a representative method of the invention for producing somatic pine embryos from loblolly pine.

Female gametophytes containing zygotic embryos were removed from seeds four to five weeks after fertilization. The seed coats were removed but the embryos were not further dissected out of the surrounding gametophyte other than to excise the nucellar end. The cones were stored at 4° C. until used. Immediately before removal of the immature embryos the seeds were sterilized utilizing an initial washing and detergent treatment followed by a ten minute sterilization in 15% $H_2O_2$. The explants were thoroughly washed with sterile distilled water after each treatment.

Tables 1 and 2 set forth the compositions of media useful for producing pine somatic embryos.

TABLE 1

Pinus Taeda Basal Medium (BM)

| Constituent | Concentration (mg/L) |
|---|---|
| $NH_4NO_3$ | 150.0 |
| $KNO_3$ | 909.9 |
| $KH_2PO_4$ | 136.1 |
| $Ca(NO_3)_2 \cdot 4H_2O$ | 236.2 |
| $CaCl_2 \cdot 4H_2O$ | 50.0 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 27.86 |
| $Na_2EDTA$ | 37.36 |
| Maltose | 30,000. |
| myo-Inositol | 200 |
| Casamino acids | 500 |
| L-Glutamine | 1000 |
| Thiamine.HCl | 1.00 |
| Pyridoxine.HCl | 0.50 |
| Nicotinic acid | 0.50 |
| Glycine | 2.00 |
| Gelrite[+] | 1600 |
| pH adjusted to 5.7 | |

[+]Used if a solid medium is desired.

TABLE 2

Composition of Media for Different Stage Treatments

| Medium | Composition |
|---|---|
| $BM_1$ - Induction Medium | BM + 2,4-D (15 µM) + Kinetin (2 µM) + BAP (2 µM). |
| $BM_2$ - Maintenance Medium | BM + 2,4-D (5 µM) + Kinetin (0.5 µM) + BAP (0.5 µM) GELRITE (1600 mg/L) is added when a solid medium is desired. |
| $BM_3$ - Development Medium | BM + 25 mg/L abscisic acid + 13% PEG-8000 + 800 mg/L additional myo-inositol + 0.1% activated charcoal. The following amino acid mixture is added: L-proline (100 mg/L), L-asparagine (100 mg/L), L-arginine (50 mg/L), L-alanine (20 mg/L), and L-serine (20 mg/L). GELRITE (2500 mg/L) is added when a solid medium is desired. |
| $BM_4$ - Maturation Medium | $BM_3$ modified by omitting maltose and PEG-8000, reducing abscisic acid to 10 g/L, and adding 2% sucrose (2%) and GELRITE (10 g/L) |
| $BM_5$ - Stratification Medium | $BM_3$ modified by omitting abscisic acid, and PEG-8000. GELRITE (2500 mg/L) is added when a solid medium is desired. |
| $BM_6$ - Germination Medium | BM modified by replacing maltose with 2% sucrose. Myo-inositol is reduced to 100.0 mg/L, glutamine and casamino acids are reduced to 0.0 mg/L. $FeSO_4 \cdot 7H_2O$ is reduced to 13.9 mg/L and $Na_2EDTA$ reduced to 18.6 mg/L. Agar at 0.8% and activated charcoal at 0.25% are added. |

Induction: Sterile gametophytes with intact embryos were placed on a solid $BM_1$ culture medium and held in an environment at 22°-25° C. with a 24 hour dark photoperiod for a time of 3-5 weeks. The length of time depends on the particular genotype being cultured. At the end of this time a white mucilaginous mass forms in association with the original explants. Microscopic examination typically reveals numerous early stage embryos associated with the mass. These are generally characterized as having a long thin-walled suspensor associated with a small head with dense cytoplasm and large nuclei.

Osmolality of the induction medium may in some instances be as high as 170 mM/kg. Normally it is about 160 mM/kg or even lower (such as 150 mM/kg).

Maintenance and Multiplication: Early stage embryos removed from the masses generated in the induction stage were first placed on a $BM_2$ gelled maintenance and multiplication medium. This differs from the induction medium in that the growth hormones (both auxins and cytokinins) are reduced by at least a full order of magnitude. Osmolality of this medium was typically raised from that of the induction medium to about 180 M/kg or higher (typically within the range of about 180-400 mM/kg for Pinus taeda) by increasing the concentration of myo-inositol to 0.5% w/v. The temperature and photoperiod were again 22°-25° C. with 24 hours in the dark. Embryos were cultured 12-14 days on the $BM_2$ solid medium before transferring to a liquid medium for further subculturing. This liquid medium has the same composition as $BM_2$, but lacks the gellant. The embryos at the end of the solid maintenance stage were typically similar in appearance to those from the induction stage. After 5 to 6 weekly subcultures on the liquid maintenance medium advanced early stage embryos have formed. These are characterized by smooth embryonal heads, estimated to typically have over 100 individual cells, with multiple suspensors.

Embryo Development: Synchronized early stage embryos were transferred to a solid development medium. The development medium either lacks growth hormones entirely, or has them present only at very low levels. Abscisic acid is typically included to facilitate further development. The further inclusion of an absorbent composition in this medium is advantageous. The absorbent composition may be chosen from a number of chemical materials having high surface area and/or controlled pore size, such as activated charcoal, soluble and insoluble forms of poly(vinyl pyrrolidone), activated alumina, and silica gel. The absorbent composition is normally present at a concentration of about 0.1-5 g/L, more generally about 0.25-2.5 g/L. Gellan gum was included at a concentration of about 0.25%.

The osmotic potential of this development medium may be raised substantially over that of the maintenance medium. It has been found advantageous to have an osmolality as high as 350 mM/kg or even higher. Development is preferably carried out in complete darkness at a temperature of 22°-25° C. until cotyledonary embryos have developed. Development time is typically several weeks, such as 7 to 10 weeks.

Maturation: After 7 to 10 weeks on development medium, cotyledonary embryos are singulated and transferred to maturation medium $BM_4$. Embryos are kept in the dark for 1 to 3 weeks at a temperature in the range of from 3° C. to 6° C.

Stratification: Cotyledonary embryos were singulated and transferred to stratification medium $BM_5$. This medium is similar to development medium but lacks abscisic acid, PEG-8000, and gellan gum. Embryos were cultivated on stratification medium at between about 1° C. and about 10° C. in the dark for between three to six weeks.

Drying: The mature embryos still on their filter paper support were lifted from the pad and placed in a closed container over $H_2O$ at a relative humidity of 97%, for a period of about three weeks.

Germination: The dried mature embryos were rehydrated by placing them, while still on the filter paper support, for about 24 hours on a pad saturated with liquid germination medium. The embryos were then placed individually on solid $BM_6$ medium for germination. This is a basal medium lacking growth hormones which has been modified by reducing sucrose, myo-inositol and organic nitrogen. The embryos were incubated on $BM_6$ medium for about 10 weeks under environmental conditions of 23°-25° C., and a 16 hour light-8 hour dark photoperiod, until the resulting plantlets have a well developed radicle and hypocotyl and green cotyledonary structure and epicotyl.

Because of the reduced carbohydrate concentration, the osmotic potential of the germination medium is further reduced below that of the development medium. It is normally below about 150 mM/kg (such as about 100 mM/kg).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for producing mature pine somatic embryos, comprising the steps of:
   (a) culturing pre-cotyledonary pine somatic embryos in, or on, a medium comprising maltose as the principal or sole source of metabolizable sugar and less than 0.5% of gellan gum to form cotyledonary pine somatic embryos; and
   (b) culturing the cotyledonary pine somatic embryos from step (a) in, or on, a maturation medium comprising between about 1% to about 6% sucrose to produce mature pine somatic embryos.

2. The method of claim 1, wherein sucrose is the sole source of metabolizable sugar in the maturation medium.

3. The method of claim 1, wherein the concentration of sucrose in the maturation medium is between about 1% to about 3%.

4. The method of claim 1, wherein the maturation medium further comprises abscisic acid.

5. The method of claim 4, wherein the concentration of abscisic acid in the maturation medium is between about 20 mg/L to about 50 mg/L.

6. The method of claim 1, wherein the cotyledonary embryos are cultured in, or on, the maturation medium for a period from about one week to about five weeks.

7. The method of claim 1, wherein the maturation medium is a liquid medium.

8. The method of claim 1, wherein the maturation medium further comprises gellan gum.

9. The method of claim 8, wherein the concentration of gellan gum in the maturation medium is between about 0.5% to about 1.5%.

10. The method of claim 1, wherein the concentration of maltose in the medium of step (a) is between about 1% to about 3%.

11. The method of claim 1, wherein the maltose is the sole source of metabolizable sugar in the medium of step (a).

12. The method of claim 1, wherein the osmolality of the medium of step (a) is from about 250 mM/Kg to about 450 mM/Kg and the osmolality of the maturation medium is from about 130 mM/Kg to about 250 mM/kg.

13. The method of claim 1, wherein the pine is Loblolly pine.

14. The method of claim 1, wherein the pine is Radiata pine.

* * * * *